US005505853A

United States Patent [19]

Satake

[11] Patent Number: 5,505,853
[45] Date of Patent: Apr. 9, 1996

[54] SERUM:PLASMA SEPARATOR AND TUBE FOR THE SEPARATION OF SERUM:PLASMA FROM CLOT:HEMOCYTE

[75] Inventor: Sunao Satake, Tokyo, Japan

[73] Assignee: Toyo Ink Manufacturing Co., Ltd., Tokyo, Japan

[21] Appl. No.: 340,456

[22] Filed: Nov. 14, 1994

Related U.S. Application Data

[63] Continuation of Ser. No. 91,280, Jul. 15, 1993, abandoned, which is a continuation-in-part of Ser. No. 907,231, Jul. 1, 1992, abandoned.

[30] Foreign Application Priority Data

Jul. 5, 1991 [JP] Japan .................................. 3-191002
Sep. 20, 1991 [JP] Japan .................................. 3-268746

[51] Int. Cl.$^6$ ................................................. B01D 21/26
[52] U.S. Cl. ........................... 210/511; 210/516; 252/60; 252/315.1; 252/315.2; 422/101; 422/102; 435/2
[58] Field of Search ...................... 210/511, 514, 210/516, 518, 782, 789; 252/60, 315.1, 315.01, 315.2, 315.5; 422/101, 102; 435/2; 156/325, 326, 327

[56] References Cited

U.S. PATENT DOCUMENTS

| | | | |
|---|---|---|---|
| 3,920,557 | 11/1975 | Ayres | 210/516 |
| 4,083,784 | 4/1978 | Zine, Jr. | 210/83 |
| 4,457,782 | 7/1984 | Honda et al. | 106/266 |
| 4,500,661 | 2/1985 | Lakshmanan | 156/334 |
| 4,524,798 | 8/1985 | Honda et al. | 106/266 |
| 4,751,001 | 6/1988 | Saunders | 210/516 |
| 4,770,779 | 9/1988 | Ichikawa et al. | 210/516 |
| 4,994,393 | 2/1991 | Pradhan et al. | 210/516 |
| 5,093,019 | 3/1992 | Tagawa et al. | 210/516 |
| 5,304,605 | 4/1994 | Murakami et al. | 252/60 |

OTHER PUBLICATIONS

Adhesion and Sealing, Mar. Issue (undated), vol. 31, No. 3, pp. 20–23, Issued by Kobunshi Kankokai.
Hawley's Condensed Chemical Dictionary, 12th Ed., R. J. Lewis, Sr. Revised, Van Nostrand Reinhold Company, New York, pp. 23 and 113 (undated).
Handbook of Pressure Sensitive Adhesive Technology, Edited by D. Satas, pp. 527–544, Van Nostrand Reinhold Company, New York (1989).
Polymer Science Dictionary, M. Alger, Elsevier Applied Science, New York (undated), p. 465.
Handbook of Adhesive Technology, A. Pizzi and K. L. Mittal Edited, Marcel. Dekker, Inc., New York (undated) pp. 241, 248–251.

*Primary Examiner*—John Kim
*Attorney, Agent, or Firm*—Wenderoth, Lind & Ponack

[57] ABSTRACT

A serum:plasma separator is provided containing a tackifier having a softening point of 70° to 150° C. and a partition-forming material. The separator prevents hemocyte from remaining in a serum portion after blood separation and prevents migration of a component having a concentration gradient between clot and serum, even when separated blood components are stored as they are in place in a tube for the separation of blood, whereby correct examination results can be obtained. The serum:plasma separator hardly undergoes a form change at room temperature and under heat and hardly shows a viscosity change even after a long period of time. Further, the serum:plasma separator has an excellent thixotropic nature free from a change in temperature, excellent cohesion and excellent adhesion to a blood separation tube. There is also provided a tube for the separation of serum:plasma from clot;hemocyte, which contains the above serum:plasma separator.

11 Claims, No Drawings

SERUM:PLASMA SEPARATOR AND TUBE FOR THE SEPARATION OF SERUM:PLASMA FROM CLOT:HEMOCYTE

This application is a continuation of now abandoned application Ser. No. 08/091,280, filed Jul. 15, 1993, which is a continuation-in-part of now abandoned application Ser. No. 07/907,231, filed Jul. 1, 1992.

BACKGROUND OF THE INVENTION

1. Field of the Invention

The present invention relates to a serum:plasma separator and a tube for the separation of serum:plasma from clot:hemocyte (referred to as a "blood separation tube" hereinafter). More specifically, it relates to a serum:plasma separator which forms a partition having a medium specific gravity between serum and clot or between plasma and hemocyte when the blood is separated into these two components on the basis of a specific gravity difference, thereby to facilitate the blood separation procedures. The invention also relates to blood separation tube formed by placing the serum:plasma separator in a one end-closed tube and closing the other end of the tube.

2. Description of Related Art

A serum:plasma separator used for conventional blood separation procedures is obtained by incorporating a specific gravity or viscosity adjusting aid such as inorganic fine particles of silica, clay, or the like or an organic gelling agent into a resin selected from a liquid silicone resin, chlorinated polybutene, polyisobutene, an acryl polymer and α-olefin/maleic acid diester polymer as main components. The resin used as a main component basically has a hydrophobic nature. The inorganic fine particles have an effect in increasing the viscosity of the serum:plasma separator and imparting the serum:plasma separator with a thixotropic nature. The organic gelling agent has an effect in increasing the viscosity of the serum:plasma separator without imparting it with a thixotropic nature.

However, when the above conventional serum:plasma separator is used for centrifugal separation, hemocyte is liable to remain above the serum:plasma separator, i.e., in serum. That is, the separation function of the above conventional serum:plasma separator is insufficient. Further, while centrifugally separated components are stored as they are in place in a separation tube, migration of components having a concentration gradient through the serum:plasma separator takes place between clot and serum or between hemocyte and plasma. Therefore, values obtained by measuring the centrifugally separated and stored blood components, such as potassium ion value, are unreliable.

Meanwhile, the resin as a main component is liquid-like. When a both end-closed tube containing the serum:plasma separator is stored by placing it horizontally, this is unpractical because the serum:plasma separator flows. In order to overcome this effect, a thixotropic aid such as finely milled mica or colloidal silica or an organic gelling agent is incorporated into the serum:plasma separator. The serum:plasma separator containing a thixotropic aid has thixotropic nature at room temperature and is prevented from flowing while it is stored. At a high temperature, however, the thixotropic nature of the serum:plasma separator decreases, and the viscosity of the serum:plasma separator also decreases. Therefore, the separation aid flows. The serum:plasma separator containing an organic gelling agent is prevented from flowing at room temperature and at a high temperature. However, the viscosity of the serum:plasma separator increases with time and the performance as a serum:plasma separator decreases.

SUMMARY OF THE INVENTION

It is an object of the present invention to provide a serum:plasma separator which prevents hemocyte from remaining in a serum portion after blood separation and prevents migration of a component having a concentration gradient between clot and serum even when separated blood components are stored as they are in place in a separation tube, whereby correct examination results can be obtained.

It is another object of the present invention to provide a serum:plasma separator which hardly undergoes a form change at room temperature and under heat and which hardly shows a viscosity change even after a long period of time.

It is further another object of the present invention to provide a serum:plasma separator which has excellent thixotropic nature free from a change in temperature, excellent cohesion and excellent adhesion to a blood separation tube.

It is still further another object of the present invention to provide a blood separation tube containing the above serum:plasma separator.

According to the present invention, there is provided a serum:plasma separator comprising a tackifier having a softening point of 70° to 150° C. and a partition-forming material.

According to the present invention, there is also provided a blood separation tube prepared by placing the above serum:plasma separator in a one end-closed tube and closing the other end.

DETAILED DESCRIPTION OF THE INVENTION

The serum:plasma separator of the present invention is obtained from a partition-forming material and a tackifier and optionally, a lipophilic laminar inorganic compound. It has a specific gravity of 1.035 to 1.060 in the intermediate region between the specific gravity of serum and that of clot or between the specific gravity of plasma and that of hemocyte. The above-defined specific gravity can be achieved by properly selecting a partition-forming material, a tackifier and optionally, a lipophilic laminar inorganic compound. It is preferred to give a large difference in the specific gravity between clot or hemocyte and the serum:plasma separator, since the larger the difference in the specific gravity is, the greater the floatability of the serum:plasma separator in centrifugal separation is. However, when the serum:plasma separator has a specific gravity of less than 1.035, undesirably, part of the serum:plasma separator is sometimes separated into serum or plasma after the centrifugal separation.

The partition-forming material used in the present invention can be selected from a wide range of materials including a variety of organic solvents having a low viscosity, plasticizers and oily polymers. Oily polymers preferably having a viscosity of 200 to 600,000 cps at 25° C. can be properly used to achieve proper flowability and proper gelation in practical use. Examples of these oily polymers include silicone, chlorinated polybutene, chlorinated polybutadiene, poly(meth)acrylate, polyisobutene and a copolymer obtained from an α-olefin or styrene and maleic acid diester.

The tackifier used in the serum:plasma separator of the present invention is generally thermoplastic and has the form of a solid at room temperature. It has a softening point of 70° to 150° C. and a weight average molecular weight of approximately 200 to 1,500. When incorporated into an oily polymer, the tackifier improves the adhesion and wettability to a blood separation tube. When the softening point of the tackifier is lower than 70° C., the serum:plasma separator is liable to flow in the blood separation tube at a relatively high temperature which may occur during the transportation thereof. That is, the storage stability of the serum:plasma separator decreases, and further, hemocyte is often liable to remain in plasma or serum. When the above softening point exceeds 150° C., the partition-forming material has too high a viscosity. For this reason, the floatability of the partition-forming material deteriorates and it is difficult to form a satisfactory partition.

The tackifier is largely classified into tackifiers derived from natural resins and tackifiers formed of synthetic resins. The tackifier refers to an additive which is to be added to a polymer to impart the polymer with tackiness.

Examples of the tackifiers derived from natural resins include rosin, dammar, polymerized rosin, partially hydrogenated rosin, glycerin ester rosin, partially hydrogenated glycerin ester rosin, completely hydrogenated glycerin ester rosin, polymerized glycerin ester rosin, pentaerythritol ester rosin, partially hydrogenated pentaerythritol ester rosin, polymerized pentaerythritol ester rosin, α-pinene, a polymer of β-pinerie, polyterpene resins such as a dipentene polymer, hydrogenated polyterpene resins, and terpene phenol.

Examples of the tackifiers formed of synthetic resins include olefin and diolefin polymers, a cyclopentadiene resin, an aromatic petroleum resin, a hydrogenation product of an aromatic resin, a phenolic resin, an alkyl phenol-acetylene resin, a styrene resin, a xylene resin, a coumarone indene resin, and a vinyl toluene-α-methylstyrene copolymer resin.

The amount of the tackifier for use in the present invention differs depending upon its compatibility with a partition-forming material and its viscosity. In general, the amount of the tackifier per 100 parts by weight of the partition-forming material is 0.1 to 60 parts by weight, preferably 1 to 30 parts by weight.

When the amount of the tackifier is less than the above lower limit, the cohesion of the serum:plasma separator and the adhesion of the serum:plasma separator to a blood separation tube are insufficient. When a lipophilic laminar inorganic compound is also incorporated, the amount of the tackifier adsorbed on the lipophilic laminar inorganic compound is too small to obtain sufficient thixotropic nature. When the amount of the tackifier is more than the above upper limit, the compatibility between the tackifier and the partition-forming material is deteriorated to cause a phase separation between these two components, or the viscosity of the serum:plasma separator increases to make the operation of centrifugal separation difficult.

The lipophilic laminar inorganic compound is prepared by replacing interlayer metal ions of clay mineral such as natural or synthetic mica, bentonite or smectite with an onium compound having a lipophilic group such as alkyl ammonium salt. The lipophilic laminar inorganic compound easily swells by taking an organic compound having a small or intermediate size into interlayer spaces. As a result, the serum:plasma separator has high thixotropy. The oil absorption properties of the lipophilic laminar inorganic compound change depending upon a temperature change, and the change in the thixotropic nature of the serum:plasma separator by a temperature change can be minimized.

The amount of the lipophilic laminar inorganic compound for use in the serum:plasma separator is determined according to the viscosity and specific gravity of the serum:plasma separator. The above amount is generally preferably 0.1 to 5 parts by weight per 100 parts by weight of the partition-forming material. When the amount of the lipophilic laminar inorganic compound is too small, sufficient thixotropic nature cannot be imparted to the serum:plasma separator, and flowing of the serum:plasma separator is caused. When this amount is too large, the serum:plasma separator shows an increase in the viscosity and specific gravity and is not suitable for practical use.

The serum:plasma separator of the present invention preferably has the following physical properties. That is, the specific gravity measured at 25° C. is between the specific gravity of serum and that of clot or between the specific gravity of plasma and that of hemocyte, i.e., 1.035 to 1.060. The viscosity is in the range of 200,000 to 2,000,000 cps.

The serum:plasma separator of the present invention may further contain an inorganic powder, an organic additive and a blood coagulant. Examples of the inorganic powder include silica, talc and alumina. Examples of the organic additive include wax, a plasticizer and a gelling agent.

The serum:plasma separator of the present invention can be produced by heating the partition-forming material up to 80° to 200° C., adding a predetermined amount of the tackifier and optionally a predetermined amount of the lipophilic laminar inorganic compound, and either stirring the resultant mixture under heat or preparing a dispersion of the resultant mixture with a roll.

The serum:plasma separator of the present invention exhibits smaller flowing with time at room temperature and under heat and a smaller change in viscosity with time than any conventional serum:plasma separator which is prepared from an inorganic powder or an organic gelling agent but does not contain a tackifier in combination. The reasons for these advantages are that the serum:plasma separator of the present invention has, unlike a conventional serum:plasma separator, thixotropic nature free from a change in temperature, cohesion and adhesion to a tube. As a result, the serum:plasma separator of the present invention hardly changes its form with time even if its viscosity is not high, and the viscosity of the serum:plasma separator of the present invention hardly changes with time.

The present invention will be detailed hereinafter by reference to Examples, in which "part" stands for "part by weight".

EXAMPLE 1

A four-necked flask was charged with 100 parts of a copolymer (viscosity at 25° C.: 2,000 cps) obtained from a mixture of an α-olefin having 12 carbon atoms with an α-olefin having 14 carbon atoms and dimethyl maleate (α-olefins/dimethyl maleate molar ratio was 1/1) and 40 parts of pentaerythritol ester of partially hydrogenated rosin (Pentalyn H, softening point 97° C., supplied by Rika Hercules), and the resultant mixture was stirred at 100° C. for 2 hours to give a serum separator having a viscosity of 2,000,000 cps and a specific gravity of 1.035. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum and that no hemocyte remained in the serum. When the test tube was stored for 7 days as it contained the separated blood components, no migration of components in a hemocyte to the serum was observed.

The viscosity values described in this Examples and those in Examples below were obtained by measurement with an E-type viscometer.

EXAMPLE 2

A four-necked flask was charged with 100 parts of a copolymer (viscosity at 25° C.: 2,000 cps) obtained from a mixture of an α-olefin having 12 carbon atoms with an α-olefin having 14 carbon atoms and dimethyl maleate (α-olefins/dimethyl maleate molar ratio was 1/1)and 10 parts of pentaerythritol ester of partially hydrogenated rosin (Pentalyn H, softening point 97° C., supplied by Rika Hercules), the resultant mixture was stirred at 100° C. for 1 hour. The so-obtained mixture and 2 parts of alkylammonium-modified natural smectite (Benton 38, supplied by NL Industry) were kneaded with a three-roll mill to give a serum separator having a viscosity of 400,000 cps and a specific gravity of 1.040. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum and that no hemocyte remained in the serum. When the test tube was stored for 7 days as it contained the separated blood components, no migration of components in hemocyte to the serum was observed. Further, 1.5 g of the above-obtained serum separator was placed in the bottom of a 15 cc test tube, and the test tube was placed horizontally in a dryer and stored there at 60° C. for 4 days. The result was that the flow length of the serum separator was not more than 2 mm.

EXAMPLE 3

A four-necked flask was charged with 100 parts of polyisobutene having a number average molecular weight of about 1,000 and a viscosity of 1,500 cps (measured at 25° C.) and 5 parts of glycerin ester of partially hydrogenated rosin (Staybelite 10, softening point 71°–78° C., supplied by Rika Hercules), and the resultant mixture was stirred at 100° C. for 1 hour. The so-obtained mixture and 2 parts of a silica powder were kneaded with a three-roll mill to give a serum separator having a viscosity of 400,000 cps and a specific gravity of 1.040. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum and that no hemocyte remained in the serum. When the test tube was stored for 7 days as it contained the separated blood components, no migration of components in a hemocyte to the serum was observed. Further, 1.5 g of the above-obtained serum separator was placed in the bottom of a 15 cc test tube, and the test tube was placed horizontally in a dryer and stored there at 60° C. for 4 days. The result was that the flow length of the serum separator was not more than 2 mm.

EXAMPLE 4

A four-necked flask was charged with 100 parts of polyisobutene having a number average molecular weight of about 1,000 and a viscosity of 1,500 cps (measured at 25° C.) and 5 parts of glycerin ester of partially hydrogenated rosin (Staybelite 10, softening point 71°–78° C., supplied by Rika Hercules), and the resultant mixture was stirred at 100° C. for 1 hour. The so-obtained mixture and 3 parts of alkylammonium-modified natural smectite (Benton 38, supplied by NL Industry) were kneaded with a three-roll mill to give a serum separator having a viscosity of 400,000 cps and a specific gravity of 1.048. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum and that no hemocyte remained in the serum. When the rest tube was stored for 7 days as it contained the separated blood components, no migration of components in hemocyte to the serum was observed. Further, 1.5 g of the above-obtained serum separator was placed in the bottom of a 15 cc test tube, and the test tube was placed horizontally in a dryer and stored there at 60° C. for 4 days. The result was that the flow length of the serum separator was not more than 2 mm.

EXAMPLE 5

100 Parts of a copolymer obtained from a mixture of an α-olefin having 12 carbon atoms with an α-olefin having 14 carbon atoms and dimethyl maleate (α-olefins/dimethyl maleate molar ratio was 1/1), 20 parts of a terpentine resin (YS resin Px #1000, softening point 100° C., supplied by Yasuhara Chemical Co., Ltd.) and 2 parts of alkylammonium-modified natural smectite (Benton 38, supplied by NL Industry) were kneaded with a three-roll mill to give a serum separator having a viscosity of 500,000 and a specific gravity of 1.042. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum and that no hemocyte remained in the serum. When the test tube was stored for 7 days as it contained the sepal-areal blood components, no migration of components in hemocyte to the serum was observed. Further, 1.5 g of the above-obtained serum separator was placed in the bottom of a 15 cc test tube, and the test tube was placed horizontally in a dryer and stored there at 60° C. for 4 days. The result was that the flow length of the serum separator was not more than 1 mm.

EXAMPLE 6

A four-necked flask was charged with 100 parts of a copolymer obtained from a mixture of an α-olefin having 12 carbon atoms with an α-olefin having 14 carbon atoms and dimethyl maleate (α-olefins/dimethyl maleate molar ratio was 1/1) as a partition-forming material and 13 parts of a petroleum resin (FTR-6110, softening point 110° C., supplied by Mitsui Petrochemicals Industries Ltd.) as a tackifier. The resultant mixture was stirred at 120° C. for 2 hours. The so-obtained mixture and 2.3 parts of alkylammonium-modified natural smectite (Benton 38, supplied by NL Industry) were kneaded with a three-roll mill to give a serum separator having a viscosity of 400,000 cps at 25° C. and a specific gravity of 1.045. The so-obtained serum separator was heated to about 60° C., about 1.7 cc of the serum separator was placed in the bottom of a 15 cc test tube with a syringe, and the test tube was tightly closed with a butyl rubber closure and vacuumed. The test tube was allowed to stand vertically at room temperature overnight, and then allowed to stand horizontally in an oven at 50° C. for 3 days to show that its flow length from its original position was not more than 2 mm. Then, 9 cc of a blood sample was also placed in the test tube and then centrifugally separated at 25° C. at 1,700 G for 10 minutes. The result was that the serum separator exactly migrated to a position between clot and serum and that a so-called hemocyte remaining (hemocyte adhering to the top portion of the separator) did not occur.

EXAMPLE 7

A four-necked flask was charged with 100 parts of polybutene (Polybutene 300R: supplied by Idemitsu Kosan Co., Ltd.) as a partition-forming material and 20 parts of a polyterpene resin (Clearon M-100, softening point 100° C., supplied by Yasuhara Chemical Industries Ltd.) as a tackifier. The resultant mixture was stirred at 100° C. for 2 hours. The so-obtained mixture and 25 parts of a precipitatable barium sulfate which had been rendered hydrophobic were kneaded with a three-roll mill to give a serum separator having a viscosity of 400,000 cps at 25° C. and a specific gravity of 1.043. The so-obtained serum separator was heated to about 60° C., 1.7 cc of the serum separator was placed in the bottom of a 15 cc test tube with a syringe, and the test tube was tightly closed with a butyl rubber closure and vacuumed. The test tube was allowed to stand vertically at room temperature overnight, and then allowed to stand horizontally in an oven at 50° C. for 3 days to show that its flow length from its original position was not more than 2 mm. Then, 9 cc of a blood sample was also placed in the test tube and then centrifugally separated at 25° C. at 1,700 G for 10 minutes. The result was that the serum separator exactly migrated to a position between clot and serum and that a so-called hemocyte remaining (hemocyte adhering to the top portion of the separator) did not occur.

EXAMPLE 8

A four-necked flask was charged with 100 parts of an α-olefin-ethylene copolymer (LUGANT HC-2000, supplied by Mitsui Petrochemicals Industries Ltd. ) as a partition-forming material and 20 parts of a petroleum resin (FTR-6110, softening point 110° C., supplied by Mitsui Petrochemicals Industries Ltd.) as a tackifier. The resultant mixture was stirred at 100° C. for 2 hours. The so-obtained mixture and 25 parts of a precipitatable barium sulfate which had been rendered hydrophobic were kneaded with a three-roll mill to give a serum separator having a viscosity of 500,000 cps at 25° C. and a specific gravity of 1.045. The so-obtained serum separator was heated to about 60° C., about 1.7 cc of the serum separator was placed in the bottom of a 15 cc test tube with a syringe, and the test tube was tightly closed with a butyl rubber closure and vacuumed. The test tube was allowed to stand vertically at room temperature overnight, and then allowed to stand horizontally in an oven at 50° C. for 3 days to show that its flow length from its original position was not more than 2 mm. Then, 9 cc of a blood sample was also placed in the test tube and then centrifugally separated at 25° C. at 1,700 G for 10 minutes. The result was that the serum separator exactly migrated to a position between clot and serum and that a so-called hemocyte remaining (hemocyte adhering to the top portion of the separator) did not occur.

COMPARATIVE EXAMPLE 1

One gram of a copolymer (viscosity at 25° C.: 2,000 cps) obtained from a mixture of an α-olefin having 12 carbon atoms with an α-olefin having 14 carbon atoms and dimethyl maleate (α-olefins/dimethyl maleate molar ratio was 1/1) was placed in a 15 cc test tube, and the test tube was tightly closed with a butyl rubber closure and vacuumed. Then, 10 cc of a blood sample was also placed in the test tube. The test tube was allowed to stand for 1 day, and then the blood was centrifugally separated at 1,200 G for 10 minutes. The result was that the serum separator was positioned between clot and serum but that hemocyte remained in the serum. When the test tube was stored for 7 days as it contained the separated blood components, migration of components in hemocyte to the serum was observed. Further, 1.5 g of the above-obtained serum separator was placed in the bottom of a 15 cc test tube, and the test tube was placed horizontally in a dryer and stored there at 60° C. for 1 hour. The result was that almost all the serum separator flowed.

COMPARATIVE EXAMPLE 2

100 Parts of a copolymer (viscosity at 25° C.: 2,000 cps) obtained from a mixture of an α-olefin having 12 carbon atoms with an α-olefin having 14 carbon atoms and dimethyl maleate (α-olefins/dimethyl maleate molar ratio was 1/1), 2.2 parts of alkylammonium-modified natural smectite (Benton 38, supplied by NL Industry) and 0.5 part of colloidal silica were kneaded with a three-roll mill to give a serum separator having a viscosity of 600,000 cps and a specific gravity of 1.045. One gram of the serum separator was placed in a 15 cc test tube, and the test tube was tightly closed with a butyl rubber closure and vacuumed. Then, 10 cc of a blood sample was also placed in the test tube. Then, the test tube was allowed to stand for 1 day, and then the blood was centrifugally separated at 1,200 G for 10 minutes. The result was that the serum separator was positioned between clot and serum but that hemocyte remained in the serum. When the test tube was stored for 7 days as it contained the separated blood components, migration of components in hemocyte to the serum was observed. Further, 1.5 g of the above-obtained serum separator was placed in the bottom of a 15 cc test tube, and the test tube was placed horizontally in a dryer and stored there at 60° C. for 1 day. The result was that the flow length of the serum separator was 8 mm.

COMPARATIVE EXAMPLE 3

100 Parts of a copolymer (viscosity at 25° C.: 2,000 cps) obtained from a mixture of an α-olefin having 12 carbon atoms with an α-olefin having 14 carbon atoms and dimethyl maleate (α-olefins/dimethyl maleate molar ratio was 1/1) and 0.5 part of a condensate obtained from sorbitol and benzaldehyde (Gelol D, supplied by Shin-Nippon Rikasha) were kneaded with a three roll mill to give a serum separator having a specific gravity of 1.050 and a viscosity of 500,000 cps. 1.5 Grams of the serum separator was placed in the bottom of a 15 cc test tube, and the test tube was tightly closed with a butyl rubber closure and vacuumed. Then, the test tube was placed horizontally in a dryer and stored there at 60° C. for 1 day to show that the flow length of the serum separator was not more than 1 mm. However, the viscosity of the serum separator increased with time, and after one year, the serum separator did not flow at all even in centrifugal separation.

COMPARATIVE EXAMPLE 4

100 Parts of a copolymer obtained from a mixture of an α-olefin having 12 carbon atoms with an α-olefin having 14 carbon atoms and dimethyl maleate (α-olefins/dimethyl maleate molar ratio was 1/1) as a partition-forming material and 2.0 parts of alkylammonium-modified natural smectite (Benton 38, supplied by NL Industry) as a thixotropic nature-imparting agent were kneaded with a three-roll mill to give a serum separator having a viscosity of 350,000 cps at 25° C. and a specific gravity of 1.045. The so-obtained serum separator was heated to about 60° C., about 1.7 cc of the serum separator was placed in the bottom of a 15 cc test tube with a syringe, and the test tube was tightly closed with a butyl rubber closure and vacuumed. The test tube was allowed to stand vertically at room temperature overnight, and then allowed to stand horizontally in an oven at 50° C. for 3 days to show that its flow length from its original position was than 40 mm or more. Further, 9 cc of a blood sample was also placed in the test tube and then centrifugally separated at 25° C. at 1,700 G for 10 minutes. The result was that the serum separator migrated to a position between clot and serum and that a so-called hemocyte remaining (hemocyte adhering to the top portion of the separator) was observed to a considerable degree.

COMPARATIVE EXAMPLE 5

A four-necked flask was charged with 100 Parts of a copolymer obtained from a mixture of an α-olefin having 12 carbon atoms with an α-olefin having 14 carbon atoms and dimethyl maleate (α-olefins/dimethyl maleate molar ratio was 1/1) as a partition-forming material and 13 parts of a polypinene resin (Zonarex Alpha 25 RESIN, softening point 28° C., supplied by Arizona Chemical) as a tackifier, and the resultant mixture was stirred at 120° C. for 2 hours. The so-obtained mixture and 2.3 parts of alkylammonium-modified natural smectite (Benton 38, supplied by NL Industry) with a three-roll mill to give a serum separator having a viscosity of 400,000 cps at 25° C. and a specific gravity of 1.045. The so-obtained serum separator was heated to about 60° C., about 1.7 cc of the serum separator was placed in the bottom of a 15 cc rest tube with a syringe, and the rest tube was tightly closed with a butyl rubber closure and vacuumed. The test tube was allowed to stand vertically at room temperature overnight, and then allowed to stand horizontally in an oven at 50° C. for 3 days to show that its flow length from its original position was than about 20 mm. Further, 9 cc of a blood sample was also placed in the test tube and then centrifugally separated at 25° C. at 1,700 G for 10 minutes. The result was that the serum separator migrated to a position between clot and serum and that a so-called hemocyte remaining (hemocyte adhering to the top portion of the separator) was observed to a considerable degree.

COMPARATIVE EXAMPLE 6

100 Parts of a copolymer obtained from a mixture of an α-olefin having 12 carbon atoms with an α-olefin having 14 carbon atoms and dimethyl maleate (α-olefins/dimethyl maleate molar ratio was 1/1) as a partition-forming material, 20 parts of a mixture of an α-olefin having 12 carbon atoms with an α-olefin having 14 carbon atoms (trade name; DIALEN, supplied by Mitsubishi Kasei Co., Ltd.) and 2.0 parts of alkylammonium-modified natural smectite (Benton 38, supplied by NL Industry) were kneaded with a three-roll mill to give a serum separator having a viscosity of 300,000 cps at 25° C. and a specific gravity of 1.042. The so-obtained serum separator was heated to about 60° C., about 1.7 cc of the serum separator was placed in the bottom of a 15 cc test tube with a syringe, and the test tube was tightly closed with a butyl rubber closure and vacuumed. The test tube was allowed to stand vertically at room temperature overnight, and then allowed to stand horizontally in an oven at 50° C. for 3 days to show that its flow length from its original position was than 40 mm or more. Further, 9 cc of a blood sample was also placed in the test tube and then centrifugally separated at 25° C. at 1,700 G for 10 minutes. The result was that the serum separator migrated to a position between clot and serum and that a so-called hemocyte remaining (hemocyte adhering to the top portion of the separator) was observed to a considerable degree.

What is claimed is:

1. A serum:plasma separator comprising a tackifier resin having a softening point of 70° to 150° C. and a partition-forming material, wherein the tackifier resin improves the adhesion of the partition-forming material to a blood separation tube.

2. A serum:plasma separator according to claim 1, wherein the tackifier resin is contained in an amount of 0.1 to 60 parts by weight per 100 parts by weight of the partition-forming material.

3. A serum:plasma separator according to claim 1, which has a specific gravity, measured at 25° C., of 1.035 to 1.060.

4. A serum:plasma separator according to claim 1, which has a viscosity, measured at 25° C., of 200,000 to 2,000,000 cps.

5. A serum:plasma separator according to claim 1, wherein the partition-forming material is an oily polymer having a viscosity, measured at 25° C., of 200 to 600,000 cps.

6. A serum:plasma separator according to claim 1, wherein the tackifier resin is a tackifier derived from a natural resin or a tackifier formed of a synthetic resin.

7. A serum:plasma separator according to claim 1, wherein a lipophilic laminar inorganic compound is further contained therein.

8. A serum:plasma separator according to claim 7, wherein the lipophilic laminar inorganic compound is contained in an amount of 0.1 to 5 parts by weight per 100 parts by weight of the partition-forming material.

9. A serum:plasma separator according to claim 7, wherein the lipophilic laminar inorganic compound is a product obtained by replacing interlayer metal ions of clay mineral with an onium compound having a lipophilic group.

10. A tube for the separation of serum:plasma from clot:hemocyte, prepared by placing the serum:plasma separator recited in claim 1 in a one end-closed tube and closing the other end.

11. A serum:plasma separating device, comprising a cylindrical tube closed at both ends and containing therein the serum:plasma separator according to claim 1.

* * * * *